(12) United States Patent
Pagan

(10) Patent No.: US 6,240,922 B1
(45) Date of Patent: Jun. 5, 2001

(54) LARYNGEAL MASK ASSEMBLIES

(75) Inventor: Eric Pagan, Hythe (GB)

(73) Assignee: Smiths Industries Public Limited Company, London (GB)

( * ) Notice: Subject to any disclaimer, the term of this patent is extended or adjusted under 35 U.S.C. 154(b) by 0 days.

(21) Appl. No.: 09/038,285

(22) Filed: Mar. 11, 1998

(30) Foreign Application Priority Data

Mar. 18, 1997 (GB) .................................................. 9705585

(51) Int. Cl.[7] .......................... A61M 16/00; A61M 16/04
(52) U.S. Cl. .................... 128/207.15; 128/200.26; 128/207.14
(58) Field of Search ................ 128/207.15, 207.14, 128/200.26; 604/96, 174

(56) References Cited

U.S. PATENT DOCUMENTS 5,896,858 * 4/1999 Brain ............................... 128/207.15
5,937,860 * 8/1999 Cook ............................... 128/207.15

FOREIGN PATENT DOCUMENTS 0 294 200   12/1988  (EP) .
2205499A    12/1988  (GB) .
97/12641    4/1997   (WO) .

* cited by examiner

Primary Examiner—Joseph Webster
(74) Attorney, Agent, or Firm—Pollock, Vande Sande & Amernick

(57) ABSTRACT

A laryngeal mask assembly has an elliptical mask portion at the patient end of a tube. The mask portion has a mount attached to the tube and a cuff extending around the periphery of the mount. The patient end of the tube opens into the center of the mount, which has three lateral ribs projecting forwardly and extending parallel and spaced from one another. The forward end of the ribs have a concave profile with rounded projections at each end. The ribs act to hold the epiglottis away from the tube opening during insertion of the assembly and to provide an air passage into the tube.

11 Claims, 2 Drawing Sheets

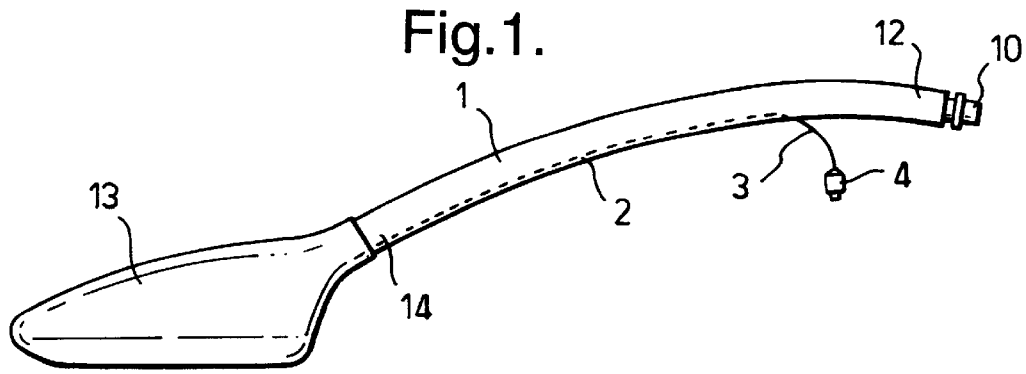
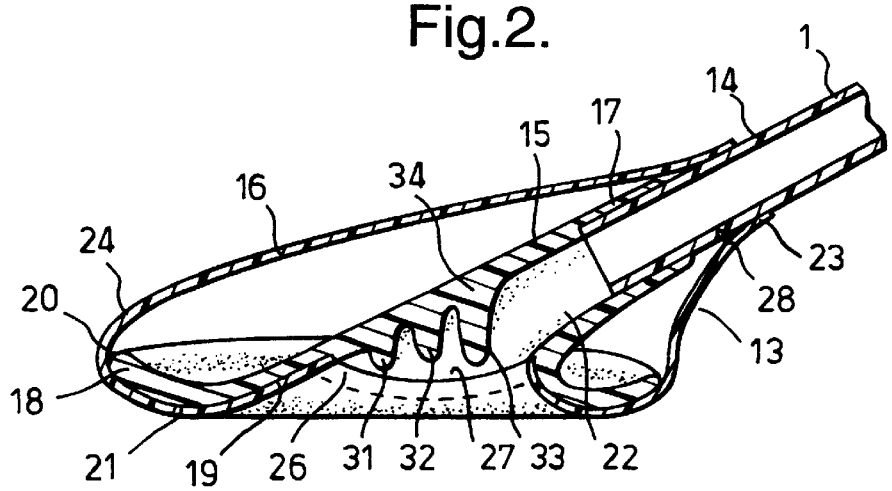
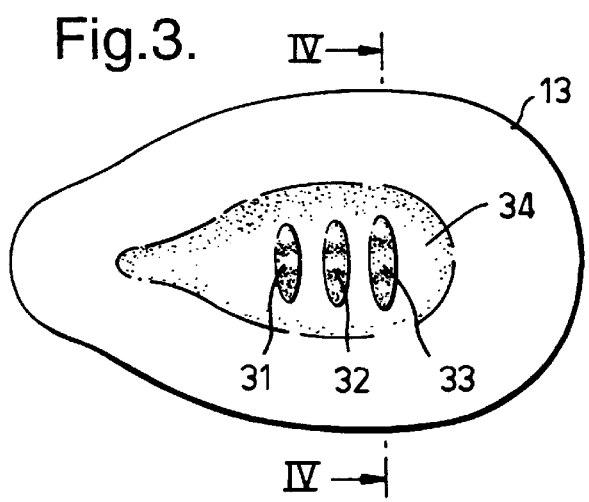
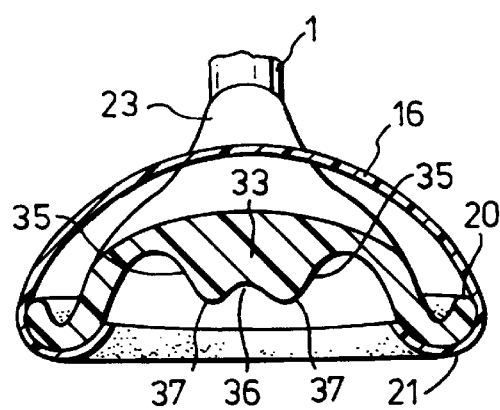

LARYNGEAL MASK ASSEMBLIES

BACKGROUND OF THE INVENTION

This invention relates to laryngeal mask assemblies

It is common practice to use an airway known as a laryngeal mask for the administration of anaesthetic and ventilation gases to a patient. These airways comprise a tube with an inflatable mask or cuff at one end, the tube being inserted in the patient's mouth so that one end is located in the hypopharynx and so that the mask forms a seal in this region with the surrounding tissue. Laryngeal masks are described in, for example, U.S. Pat. Nos. 5,355,879, 5,305, 743, 5,297,547, 5,282,464, GB 2267034, U.S. Pat. Nos. 5,249,571, 5,241,956, 5,303,697, GB 2249959, GB 2111394, EP 448878, U.S. Pat. No. 4,995,388, GB 2205499, GB 2128561 and GB 2298797.

Laryngeal masks have several advantages over endotracheal tubes, which are longer and seal with the trachea below the vocal folds. One problem with laryngeal mask airways, however, is that there is a risk that the epiglottis can enter the air passage through the airway during insertion, thereby causing a blockage. In GB-A-2205499 there is described a laryngeal mask having bars extending across the patient-end opening of the tube into the mask, to prevent the epiglottis from entering the opening.

SUMMARY OF THE PRESENT INVENTION

It is an object of the present invention to provide an improved laryngeal mask assembly.

According to the present invention there is provided a laryngeal mask assembly comprising a tube with a mask portion at its patient end, the tube opening into the center of the mask portion and the mask portion having a generally elliptical shape, the mask assembly having at least one member projecting down from the roof of the center of the mask portion, so as to deflect the epiglottis away from the opening of the tube during insertion of the assembly.

The at least one projecting member may be a rib extending laterally of the major axis of the elliptical shape of the mask portion. The lower end of each rib preferably has a concave profile with rounded projections at opposite ends. Alternatively, each projecting member may be a rib extending parallel to the major axis of the elliptical shape of the mask portion. The assembly may include three projecting members. In another arrangement, each projecting member may be a tooth with a rounded lower end. The mask portion preferably comprises a mount member attached with the tube and a cuff member attached with the mount member, the or each projecting member being molded with the mount member.

A laryngeal mask airway assembly according to the present invention, will now be described, by way of example, with reference to the accompanying drawings.

BRIEF DESCRIPTION OF THE DRAWINGS

FIG. 1 is a side elevation view of the assembly;

FIG. 2 is a sectional side elevation view of the patient end of the assembly to an enlarged scale;

FIG. 3 is a view from below of the patient end of the assembly;

FIG. 4 is a transverse sectional view along the line IV—IV of FIG. 3;

DETAILED DESCRIPTION OF THE PREFERRED EMBODIMENTS

Figure 5:
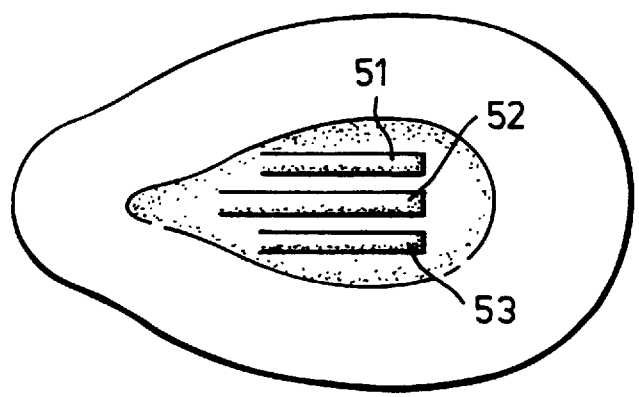
FIG. 5 is a view from below of the patient end of an alternative assembly.

With reference to FIGS. 1 to 4, the assembly comprises a bendable tube 1 of a plastics material, such as PVC, with a coupling 10 at its machine end 12. The tube 1 is curved along its length and has a mask portion 13 at its patient end 14.

The tube 1 is extruded with an inflation lumen 2 within its wall. The lumen 2 is connected towards the machine end of the assembly to an inflation line 3 with an inflation indicator and connector 4. The opposite, patient end of the inflation lumen 2 opens into the mask portion 13.

The mask portion 13 comprises a mount member 15 and a flexible bag member 16. The mount member 15 is moulded from a bendable plastics material, such as PVC. The mount member 15 has a hollow cylindrical sleeve 17 at its rear end, in which the forward, patient end 14 of the tube 1 is inserted and joined. The forward, patient end 18 of the mount member 15 is of an inverted dish shape with a generally elliptical or egg-shaped outline and with a concave recess 19. The peripheral edge 20 of the mount member 15 is curved rearwardly to form a convex peripheral forward surface 21 lying on a flat plane inclined at an angle of about 30° to the axis of the patient end of the tube 1. The sleeve 17 has a bore 22 communicating with the passage through the tube 1, at its rear end, and opening into the recess 19 at its forward end.

The bag member 16 is blow molded from a flexible, resilient plastics material, such as PVC, polyurethane, silicone, EVA, TPE, polyether block amide or the like. The bag 16 has a sock shape with an open ankle or neck portion 23 at its upper, rear end and an egg-shape lower, forward foot portion 24 shaped with the same general outline as the mount member 15. The bag 16 encompasses the forward end of the assembly, enclosing the entirety of the mount 15 and having its neck 23 attached to the outside of the forward end 14 of the tube 1, such as by solvent, adhesive or welding. The bag 16 is also attached to the concave recess 19 of the mount 15 along an annular band 26 extending around the opening of the bore 22, to seal the bag material to the mount. A hole 27 in the bag 16 provides access to the bore 22 in the mount member 15. The bag 16 provides an inflatable cuff at the forward end of the assembly and communicates with the inflation lumen 2 by means of an opening 28 cut through the outer surface of the tube 1 below the point where the bag is attached to the tube.

The mount member 15 also has, molded with it, an epiglottis deflector provided by three stiff ribs 31 to 33, or similar members, projecting down from the roof 34 of the recess 19. Each rib 31 to 33 extends laterally (that is, at right angles to the major axis of the elliptical shape of the mask portion) across only the central part of the mount member and has inclined sides 35 and a concave central region 36 forming two rounded projections 37. The ribs are spaced from one another axially along the central part of the mount member 15 and project down about half the distance between the roof 34 and the forward surface 21. The deflector acts to deflect the epiglottis during insertion of the mask assembly. The epiglottis is kept away from the roof 34 of the recess 19 in a region of the recess that is wider than the epiglottis so that there is always an air passage between the epiglottis and the inside of the mask portion 13. The gaps between adjacent ribs 31 to 33, and the gaps between the ribs and the inside of the recess 19, ensure that air is free to flow around the ribs into and out of the tube 1 but they are too small to allow the epiglottis to enter the bore 22 and block passage of air along the tube. The deflector allows a suction catheter, or the like to be inserted along the tube 1 and project from the mask portion.

Figure 6:
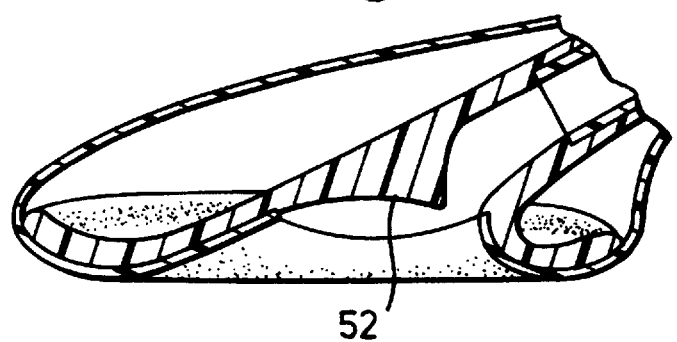
FIG. 6 is a sectional side elevation view of the patient end of the assembly shown in FIG. 5.

Various alternative forms of deflector are possible. For example, as shown in FIGS. 5 and 6, the deflector ribs 51 to 53 could be aligned longitudinally, that is parallel to the major axis of the elliptical shape of the mask portion. In such an arrangement, the forward end of the ribs is inclined smoothly from the roof of the recess.

Figure 7:
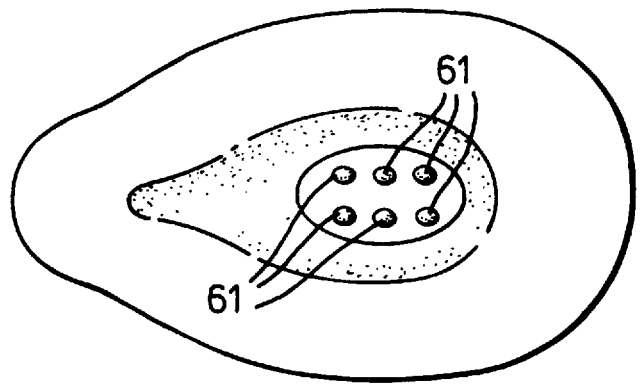
FIG. 7 is a view from below of another alternative assembly.

Another arrangement is shown in FIG. 7 in which the deflector takes the form of a group of six downwardly-projecting teeth 61 arranged in two rows of three teeth. The lower end of the teeth 61 are rounded to make them atraumatic to the epiglottis, as it slides over the end of the teeth.

What I claim is:

1. A laryngeal mask assembly comprising: a tube with a forward, patient end and a rear, machine end; a mask portion at the patient end of said tube, said mask portion having a generally elliptical shape, and said tube opening into the center of said mask, said forwardly-projecting member being exposed for direct contact with the epiglottis so that the epiglottis is deflected away from the opening of said tube solely by the action of insertion of said assembly into a patient.

2. A laryngeal mask assembly according to claim 1, wherein said projecting member is a rib extending laterally of a major axis of the elliptical shape of said mask portion.

3. A laryngeal mask assembly according to claim 2, wherein said rib has a forward end with a concave profile and rounded projections at opposite ends.

4. A laryngeal mask assembly according to claim 1, wherein said projecting member is a rib extending parallel to a major axis of the elliptical shape of said mask portion.

5. A laryngeal mask assembly according to claim 1, including three said projecting members.

6. A laryngeal mask assembly according to claim 1, wherein said projecting member is a tooth with a rounded lower end.

7. A laryngeal mask assembly according to claim 1, wherein said mask portion comprises a mount member attached with said tube and a cuff member attached with said mount member, and wherein said projecting member is moulded with said mount member.

8. A laryngeal mask assembly comprising: a tube with a forward, patient end and a rear, machine end; a mask portion at said patient end of said tube, said tube opening into a center of said mask portion and said mask portion having a generally elliptical shape and a plurality of ribs projecting forwardly on said mask portion and extending parallel with and spaced apart from one another, said ribs being exposed for direct contact with the epiglottis, so as to form a gas passage between said ribs to said tube if a forward end of said ribs is engaged by the epiglottis during insertion of said assembly to a patient, and so that the epiglottis is deflected away from the opening of said tube solely by the action of insertion of said assembly into a patient.

9. A laryngeal mask assembly comprising: a tube with a forward, patient end and a rear, machine end; and a mask portion, said mask portion including a mount member of elliptical shape attached at the patient end of said tube, and a cuff member extending around a periphery of said mask portion, wherein said mount member has an opening communicating with the patient end of said tube and a plurality of forwardly-projecting members exposed to contact the epiglottis directly so that the epiglottis is deflected away from the opening into said tube solely by the action of insertion of the assembly and so that the forwardly-projecting members ensure a gas passage into said tube around said projecting members during insertion of said assembly into a patient.

10. A laryngeal mask assembly according to claim 9, wherein said projecting members are parallel ribs.

11. A laryngeal mask assembly according to claim 9, wherein said projecting members are teeth with rounded ends.

* * * * *